(12) United States Patent
Giard, Jr. et al.

(10) Patent No.: US 6,994,213 B2
(45) Date of Patent: Feb. 7, 2006

(54) PACKAGING FOR PUSH BUTTON BLOOD COLLECTION SET

(75) Inventors: John A. Giard, Jr., Edgewater, NJ (US); Volker Niermann, Little Falls, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 201 days.

(21) Appl. No.: 10/229,740

(22) Filed: Aug. 28, 2002

(65) Prior Publication Data

US 2003/0062281 A1 Apr. 3, 2003

Related U.S. Application Data

(60) Provisional application No. 60/323,155, filed on Sep. 18, 2001.

(51) Int. Cl.
*B65D 83/10* (2006.01)

(52) U.S. Cl. ........................ 206/363; 206/480
(58) Field of Classification Search . 206/363–365,368, 206/370, 477–478, 480, 438; 604/171, 110, 604/198
See application file for complete search history.

(56) References Cited

U.S. PATENT DOCUMENTS

| | | | |
|---|---|---|---|
| 2,720,969 A | 10/1955 | Kendall | |
| 3,013,656 A | 12/1961 | Murphy | |
| 3,035,691 A | 5/1962 | Rasmussen et al. | |
| 3,485,352 A * | 12/1969 | Pilger | 206/365 |
| 3,696,920 A | 10/1972 | Lahay | |
| 3,750,875 A | 8/1973 | Juster | |
| 3,952,873 A | 4/1976 | Pampuch et al. | 206/528 |
| 4,019,633 A | 4/1977 | Roth | 206/364 |
| 4,184,593 A | 1/1980 | Dorr | 206/365 |
| 4,216,860 A | 8/1980 | Heimann | 206/370 |
| 4,332,322 A | 6/1982 | Jaeschke et al. | 206/364 |
| 4,438,845 A | 3/1984 | Mochow | 206/366 |
| 4,592,744 A | 6/1986 | Jagger et al. | |
| 4,731,059 A | 3/1988 | Wanderer et al. | |
| 4,747,831 A | 5/1988 | Kulli | |
| 4,846,808 A | 7/1989 | Haber et al. | |
| 4,850,374 A | 7/1989 | Diaz-Ramos | |
| 4,871,355 A | 10/1989 | Kikkawa | |
| 4,900,307 A | 2/1990 | Kulli | |
| 4,942,881 A | 7/1990 | Al-Sioufi et al. | |
| 4,988,339 A | 1/1991 | Vadher | |

(Continued)

FOREIGN PATENT DOCUMENTS

WO WO 99/23947 5/1999

(Continued)

*Primary Examiner*—Bryon P. Gehman
(74) *Attorney, Agent, or Firm*—Scott Rittman, Esq.; Mark Lindsey

(57) ABSTRACT

A package is provided for a medical device that a spring-driven button-actuated safety shield. The package includes a tray with a bottom wall and sidewall enclosure that extends upwardly from the bottom wall a distance greater than the height or thickness of the medical device. A flange extends outwardly from edges of the sidewall enclosure opposite the bottom wall. At least two gripping towers are formed unitarily with the bottom wall and project upwardly a distance greater than the thickness or height of the medical implement. Gripping towers are spaced from one another and are configured to grippingly engage the medical implement on opposite respective sides of the actuating button for preventing inadvertent actuation of the safety shield while the medical implement is in the tray. A cover extends removably across the flange and is supported by the gripping towers.

14 Claims, 6 Drawing Sheets

U.S. PATENT DOCUMENTS

| | | |
|---|---|---|
| 4,991,601 A | 2/1991 | Kazai et al. |
| 4,993,426 A | 2/1991 | Spencer |
| 4,994,034 A | 2/1991 | Botich et al. |
| 5,030,209 A | 7/1991 | Wanderer et al. |
| 5,031,775 A | 7/1991 | Kane .......................... 206/571 |
| 5,062,837 A | 11/1991 | Al-Sioufi et al. |
| 5,067,490 A | 11/1991 | Haber |
| 5,069,225 A | 12/1991 | Okamura |
| RE33,952 E | 6/1992 | Bonaldo |
| 5,120,311 A | 6/1992 | Sagstetter et al. |
| 5,188,599 A | 2/1993 | Botich et al. |
| 5,217,025 A | 6/1993 | Okamura |
| 5,219,333 A | 6/1993 | Sagstetter et al. |
| 5,284,244 A * | 2/1994 | O'Toole et al. ............. 206/363 |
| 5,300,039 A | 4/1994 | Poulsen |
| 5,392,918 A | 2/1995 | Harrison .................... 206/571 |
| 5,407,070 A | 4/1995 | Bascos et al. ............. 206/365 |
| 5,407,431 A | 4/1995 | Botich et al. |
| 5,413,083 A | 5/1995 | Jones |
| 5,485,917 A | 1/1996 | Early ......................... 206/363 |
| 5,501,675 A * | 3/1996 | Erskine ..................... 604/171 |
| 5,527,294 A | 6/1996 | Weatherford et al. |
| 5,540,651 A | 7/1996 | Risch et al. |
| 5,613,500 A | 3/1997 | Bishop |
| 5,616,135 A | 4/1997 | Thorne et al. |
| 5,616,136 A | 4/1997 | Shillington et al. |
| 5,637,101 A | 6/1997 | Shillington |
| 5,685,863 A | 11/1997 | Botich et al. |
| 5,690,222 A | 11/1997 | Peters ........................ 206/339 |
| 5,693,028 A | 12/1997 | Shillington |
| 5,755,673 A | 5/1998 | Kinsey |
| 5,769,826 A | 6/1998 | Johnson et al. |
| 5,797,490 A | 8/1998 | Fujii et al. |
| 5,800,395 A | 9/1998 | Botich et al. |
| 5,800,404 A | 9/1998 | Poulsen |
| 5,810,775 A | 9/1998 | Shaw |
| 5,947,284 A | 9/1999 | Foster ........................ 206/364 |
| 6,004,278 A | 12/1999 | Botich et al. |
| 6,024,727 A | 2/2000 | Thorne et al. |
| 6,047,826 A * | 4/2000 | Kalinski et al. ............ 206/365 |
| 6,063,040 A | 5/2000 | Owen et al. |
| 6,068,121 A * | 5/2000 | McGlinch ................... 206/364 |
| 6,074,373 A | 6/2000 | Sudo et al. |
| 6,077,244 A | 6/2000 | Botich et al. |
| 6,090,078 A | 7/2000 | Erskine |
| 6,096,005 A | 8/2000 | Botich et al. |
| 6,127,320 A | 10/2000 | van Ooij et al. |
| 6,146,337 A | 11/2000 | Polidoro et al. |
| 6,210,371 B1 | 4/2001 | Shaw |
| 2003/0199830 A1 * | 10/2003 | Nguyen ...................... 604/171 |

FOREIGN PATENT DOCUMENTS

| | | |
|---|---|---|
| WO | WO 00/12160 | 3/2000 |
| WO | WO 00/47256 | 8/2000 |
| WO | WO 03/015855 | 2/2003 |

\* cited by examiner

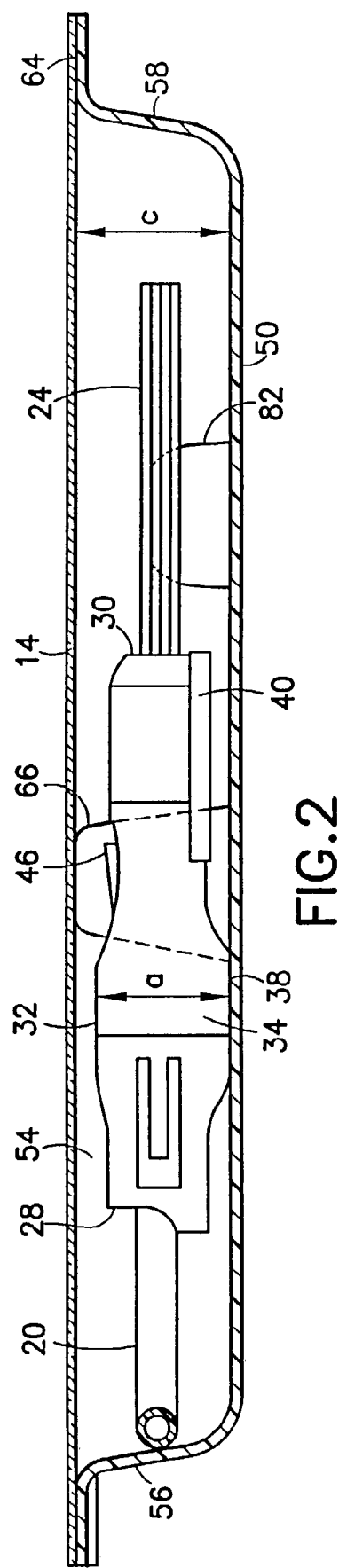
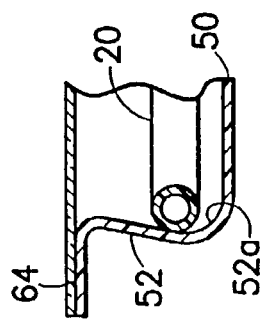

US 6,994,213 B2

PACKAGING FOR PUSH BUTTON BLOOD COLLECTION SET

This application claims priority of U.S. Provisional Patent Application No. 60/323,155 filed Sep. 18, 2001.

BACKGROUND OF THE INVENTION

1. Field of the Invention

The subject invention relates to packaging for a push button blood collection set and to the assembly of a push button blood collection set and its package. The invention also relates to a method for packaging a push button blood collection set.

2. Description of the Related Art

A push button blood collection set is used to access a blood vessel of a patient and to draw blood from a patient. The blood collection set includes a needle cannula with a proximal end, a sharply pointed distal end and a lumen extending between the ends. The proximal end of the needle cannula is permanently mounted to a plastic hub. The hub is formed with an axial passage that communicates with the lumen through the needle cannula. Flexible tubing of appropriate length is mounted to the end of the hub opposite the needle cannula, and a fitting is mounted to the end of the plastic tubing remote from the needle hub. The fitting may be configured for mating with a container, such as an evacuated blood collection tube or a blood bag. Thus, the blood collection set can be used to deliver a sample of blood from a patient to a container.

Many blood collection sets include a safety shield that is retained in a proximal position on the needle hub prior to use of the blood collection set. After use, however, the safety shield is slid distally relative to the needle hub and into a position where the safety shield surrounds the needle cannula. Some such shielding operations are carried out manually. Thus, the user may hold the proximal end of the hub and/or the plastic tubing in one hand and may slide the shield distally with the other hand. The shield locks with structure on the hub to prevent the shield from sliding completely off the hub and to prevent reexposure of the needle cannula.

More recent developments in blood collection sets include automatically actuated safety shields. For example, a spring may be disposed between the needle hub and the safety shield. A latch retains the safety shield in the proximal position on the hub and against the force of the spring. However, a push button actuator releases the latch in response to digital pressure by the user. The spring then propels the shield distally and into a shielding disposition around the needle cannula.

Many medical devices, including blood collection sets, are packaged in sterile blister packages. The typical prior art blister package includes a plastic tray for storing the medical device and a plastic cover removably secured across peripheral regions of the tray.

Prior art blister packages are not structurally sturdy. Thus, there is a significant possibility that the actuator button of the blood collection set will be triggered inadvertently by forces exerted on the blister package during storage or shipment or by forces generated when a user manually grips a blister package.

An inadvertent depression of the actuator button will urge the shield distally relative to the needle cannula and will lock the shield in a position that prevents or complicates further use of the needle cannula. Thus, an unused blood collection set may have to be discarded due to an inadvertent actuation of the safety shield caused by ordinary gripping of the blister package in which the blood collection set is sealed.

The fitting at the end of the plastic tube opposite the needle hub may include a second needle cannula that can be urged through the seal of an evacuated blood collection tube. Forces on the blister package could deform the blister package sufficiently for the needle to be urged through either the walls of the tray or through the plastic cover of the blister package. A protruding needle cannula would create the risk for an accidental needle stick.

Prior art blood collection sets typically require a band to maintain the tubing in an orderly coil within the confines of the blister package. The band works well, but adds to the cost and time to complete the packaging.

SUMMARY OF THE INVENTION

The subject invention is directed to a blister package assembly for a blood collection set and to an assembly of a blood collection set and a blister package. The subject invention further is directed to a method for packaging a blood collection set.

In one embodiment, the blood collection set includes a needle assembly that comprises a needle cannula. The needle cannula has a proximal end, a sharply pointed distal end and a lumen extending between the ends. The needle assembly further includes a plastic hub with a proximal end, a distal end and a passage extending between the ends. The proximal end of the needle cannula is securely mounted in the distal end of the hub. Thus, the lumen through the needle cannula communicates with the passage through the needle hub.

The needle assembly, in this embodiment, further includes a safety cap with a rigid tubular sidewall and an open proximal end. The open proximal end of the safety cap is telescoped in a distal-to-proximal direction over the needle cannula and is retained frictionally in proximity to the needle hub. However, the safety cap can be separated from the hub to expose the needle cannula immediately prior to use. The needle assembly also includes a safety shield that is telescoped over the needle hub. The safety shield is characterized by oppositely directed flexible wings. The wings can be folded into face-to-face engagement with one another to facilitate digital manipulation of the needle assembly. Alternatively, the wings can be taped into face-to-face engagement with the skin of a patient. The safety shield can be moved from a proximal position where the needle cannula is exposed to a distal position where the needle cannula is protectively enclosed within the safety shield. Locking structures are provided on the hub and the safety shield to prevent movement of the safety shield distally beyond the needle cannula. Additionally, locking structures are provided to prevent reexposure of a properly shielded needle cannula.

The safety shield of this embodiment is characterized by an actuating window. A resiliently deflectable actuating button projects from the needle hub and passes into the actuating window when the safety shield is in its proximal position. Release of the resiliently deflectable actuating button from the actuating window permits the needle cannula to move to the proximal position.

The needle assembly further comprises a spring disposed between a portion of the needle hub and the safety shield. The spring is disposed to retain stored energy when the needle cannula is in its distal position. However, disengagement of the actuating button from the actuating window releases the stored energy in the spring and enables the spring to propel the cannula into its proximal position surrounding the needle cannula.

The blood collection set of the embodiment further includes a length of flexible tubing with a proximal end and a distal end. The distal end of the flexible tubing is securely connected to the proximal end of the needle hub. The blood collection set also includes a fitting securely mounted to the distal end of the flexible tubing. The fitting may be configured to engage another fitting or to receive a second needle cannula. Alternatively, the fitting may have a second needle cannula permanently mounted thereon and engageable with an evacuated blood collection tube. While the package of the invention is particularly useful with push button type blood collection sets, the package is useful for a variety of blood collections sets.

A blister package according to an embodiment of the subject invention includes a tray that is molded unitarily from a plastic material such as PVC or PETG. The tray includes a bottom wall, a plurality of unitarily joined sidewalls extending away from the bottom wall and a peripheral flange extending outwardly from the sidewalls and generally parallel to the bottom wall. The distance between the peripheral flange and the bottom wall exceeds the maximum cross-sectional dimension of the needle assembly and the fitting. At least one sidewall may include an overhang spaced from the bottom wall. Thus, at least one sidewall may define a concave region for holding the tubing of the blood collection set within the tray and substantially adjacent the bottom wall.

The tray is further characterized by a plurality of towers projecting unitarily upwardly from the bottom wall. The towers comprise at least first and second gripping towers that are spaced apart sufficiently for gripping opposed sides of the needle shield in proximity to the actuating button. The gripping towers may be tapered from a major cross-sectional dimension adjacent the bottom wall to a minor cross-sectional dimension further from the bottom wall. Additionally, the gripping towers may have opposed facing convex surfaces that are configured to deflect as the safety shield of the needle assembly is urged between the gripping towers.

The gripping towers define a height greater than the maximum cross-sectional dimension of the safety shield in proximity to the actuator button. In a preferred embodiment, the upper ends of the gripping towers are substantially coplanar with the peripheral flange of the tray. Thus, the gripping towers surround and hold portions of the safety shield that contain the actuating window and the actuating button. Furthermore, the gripping towers extend sufficiently above the actuating button to prevent inadvertent actuation. The tapered configuration of the gripping towers and the convex walls of the gripping towers contribute to the strength of the gripping towers and prevent any local collapsing of the blister package that could inadvertently actuate the safety shield.

The tray of the blister package may further include at least one additional tower at a location spaced from the gripping towers. The additional tower may be disposed to position the fitting at the end of the plastic tubing remote from the needle assembly.

The blister package further includes a cover that extends unitarily across the peripheral flange of the tray. The cover preferably is formed from a flexible plastic material that can be peeled away from the peripheral flange to access the blood collection set stored therein.

The invention further is directed to a method for packaging a blood collection set such as a push button actuated. The method comprises providing a tray with a bottom wall, upstanding sidewalls extending from the bottom wall and a peripheral flange at portions of the sidewalls spaced from the bottom wall. The bottom wall of the tray includes at least first and second spaced apart gripping towers. The method further includes inserting the needle assembly of the blood collection set between the gripping towers of the tray so that the actuating button of the needle assembly is between the gripping towers and below upper ends of the gripping towers. The method proceeds by winding the plastic tubing of the blood collection set around the needle assembly and in the tray. A portion of the tubing may be gripped in a concave region of the sidewall and held reasably adjacent the bottom wall. The method concludes by adhering, bonding or otherwise attaching a removable cover across the peripheral flange of the tray for safely enclosing the blood collection set in the tray.

The blister design also has the added benefit of orientating the push button blood collection set in the blister and between the towers in such a way as to facilitate removal and prevent activation during removal. The location of the towers relative to the push button and shield are such that the user is guided to remove the pbbcs by graphing either the wings or proximal shield. This prevents the button from being activated during removal and orientates the pbbcs in the hand for immediate use.

DESCRIPTION OF THE DRAWINGS

FIG. 2 is a cross-sectional view taken along line 2—2 in FIG. 1.

FIG. 3 is a cross-sectional view taken along line 3—3 in FIG. 1.

DETAILED DESCRIPTION

Figure 1A:
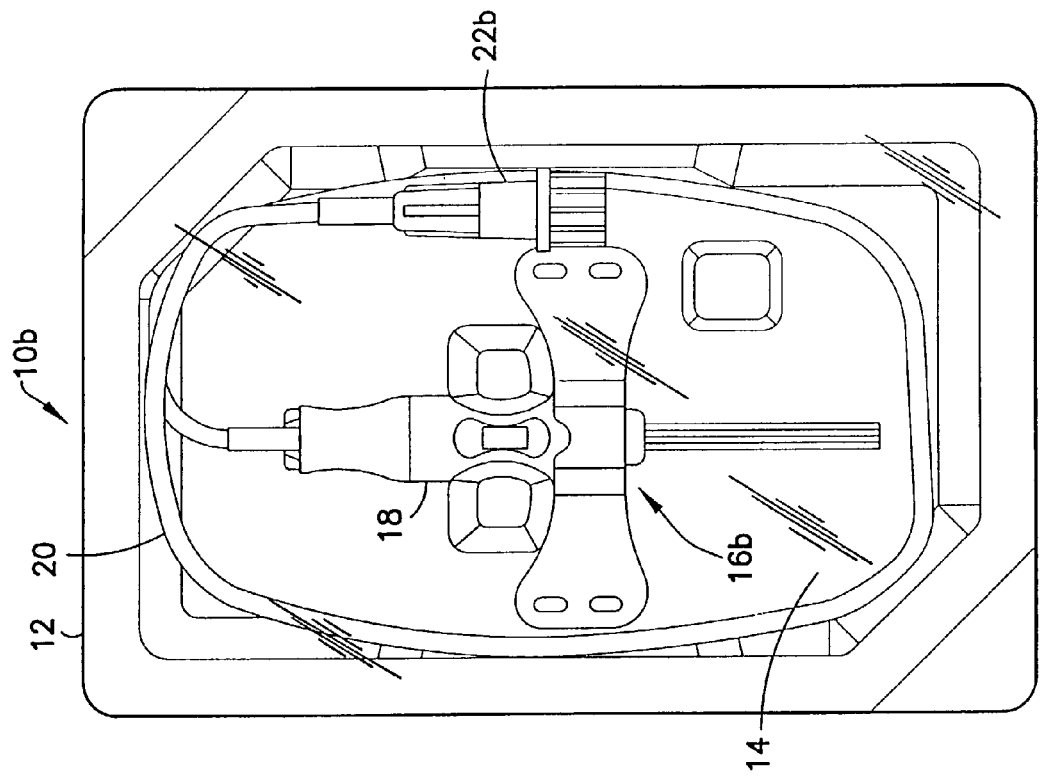
FIG. 1A is a top plan view of a blister package in accordance with the subject invention.

A first blister package in accordance with the subject invention is identified generally by the numeral 10a in FIG. 1A. Blister package 10a includes a tray 12, a cover 14 and blood collection set 16a.

Blood collection set 16a includes a needle assembly 18, a length of flexible tubing 20 and a fitting 22a. Needle assembly 18 includes a needle cannula and a needle hub, neither of which are illustrated. However, both may be of conventional prior art design. Needle assembly 18 further has a rigid tubular safety cap 24 telescoped over the needle cannula and frictionally engaged on the needle hub. Safety cap 24 can be removed from needle assembly 18 by pulling safety cap 24 away from remaining portions of needle assembly 18 to expose the needle cannula.

Needle assembly 18 further includes a safety shield 26. Safety shield 26 is a generally tubular structure with a proximal end 28, a distal end 30 and a hollow space between ends 28 and 30 for accommodating the needle hub and/or portions of the needle cannula. Safety shield 26 includes a top 32, sides 34 and 36 and a bottom 38 as shown in FIGS. 1A and 2. The terms top and bottom are not intended to imply a required gravitational orientation, but are provided merely for reference. Flexible wings 40 and 42 project transversely from safety shield 26 at locations near proximal end 30 and from portions of sides 34 and 36 adjacent bottom 38 of safety shield 26. Wings 40 and 42 can be folded into face-to-face engagement for facilitating digital manipulation of needle assembly 18. Alternatively, wings 40 and 42 can be laid flat taped against the skin of a patient.

Safety shield 26 further includes an actuating opening 44 that extends through top 32 of safety shield 26 at a location proximally of wings 40 and 42. An actuating button 46 extends from the needle hub and is engaged in actuating opening 44. Actuating button 46 holds safety shield 26 in the fixed position relative to the needle hub and the needle cannula illustrated in FIG. 1A. However, actuating button 46 can be depressed relative to needle shield 26 to release needle shield 26 from the needle hub and the needle cannula. Needle assembly 18 further includes a coil spring disposed in safety shield 26 and surrounding the needle hub. The spring functions to propel the needle hub proximally within the assembly 18.

Safety shield 26 is cross-sectionally reduced in portions adjacent actuating opening 44 as shown in FIGS. 1 and 2. The cross-sectional reduction includes concave arcuate reductions around all sides of safety shield 26 to facilitate the manipulation and actuation of needle assembly 18. Needle shield 26 defines a maximum height "a" as shown in FIG. 2. However, as shown in FIG. 2, actuating button 46 is recessed relative to portions of needle shield 26 defining maximum height "a". Needle shield 26 further defines a minimum width "b" at locations aligned with actuating opening 44, as shown in FIG. 1A.

Figure 1B:
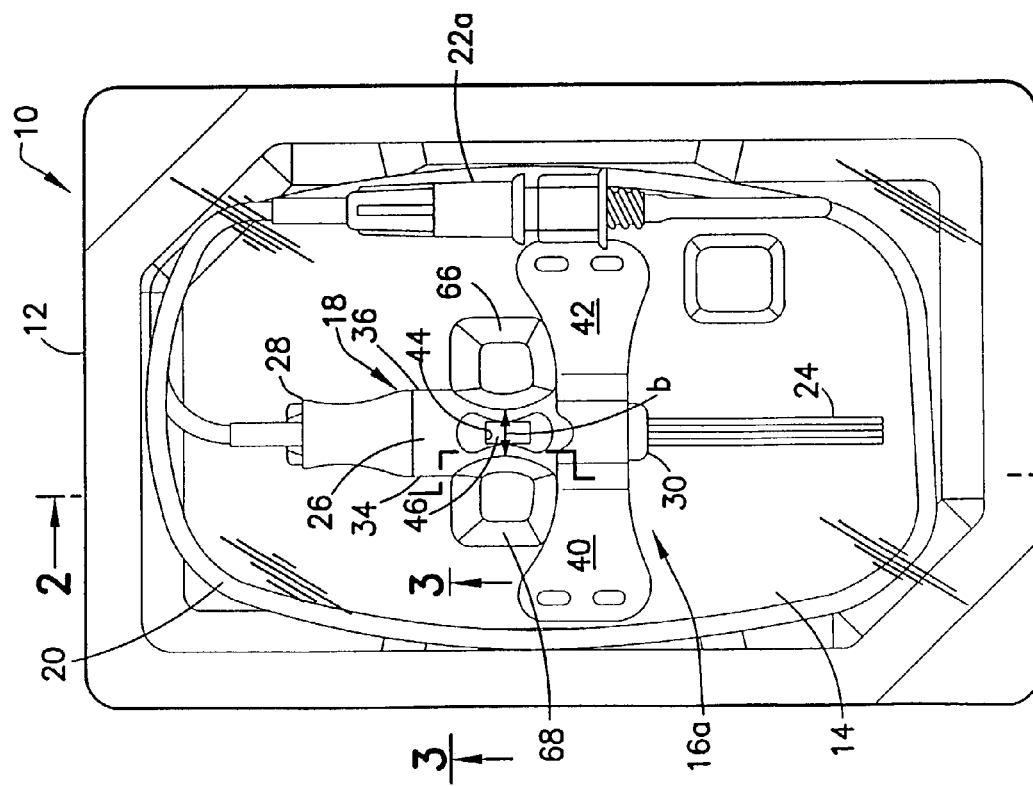
FIG. 1B is a top plan view of a second blister package in accordance with the invention.
Figure 4:
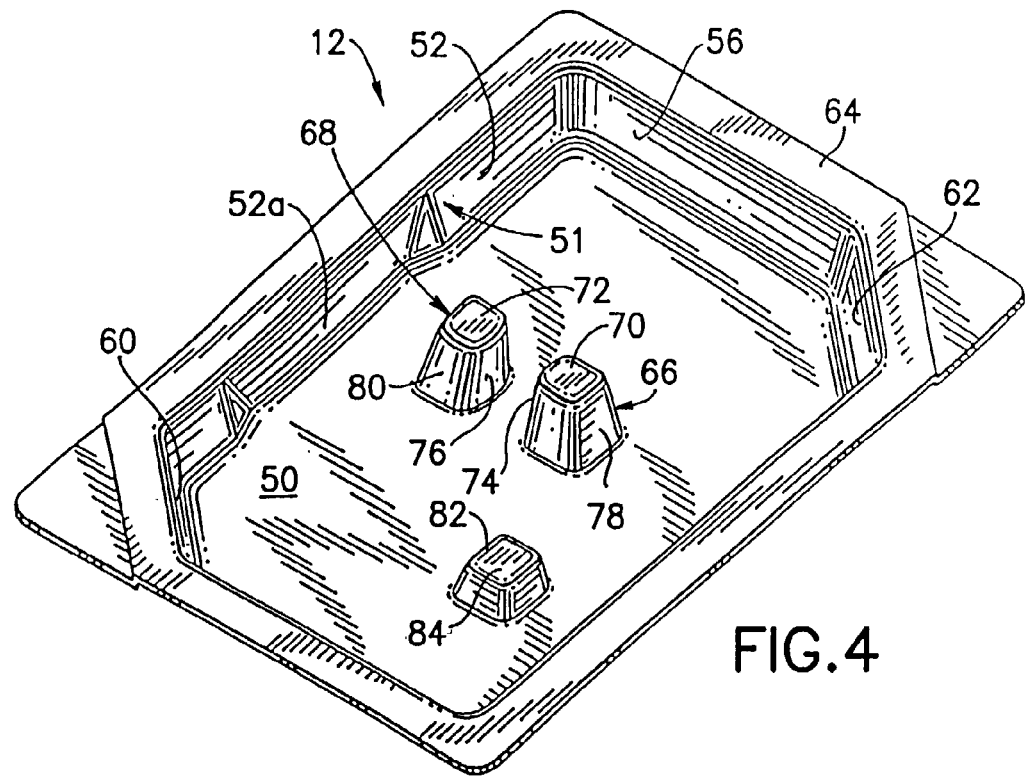
FIG. 4 is a perspective view of a tray of a blister package in accordance with the subject invention.
Figure 5:
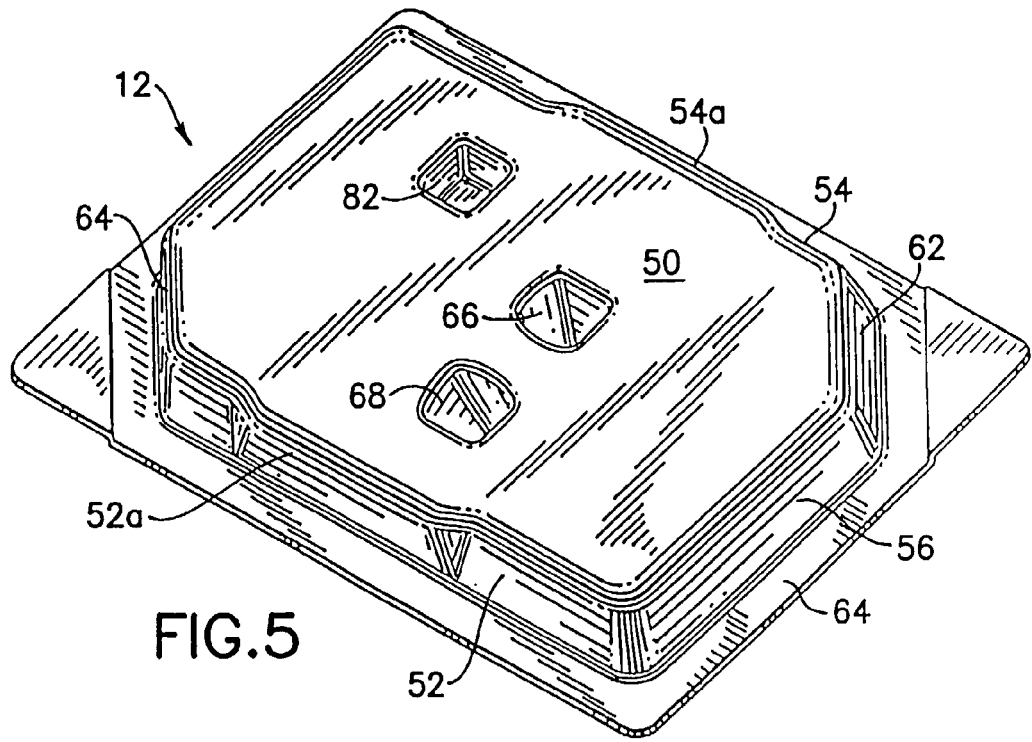
FIG. 5 is a perspective view of the bottom of the tray shown in FIG. 3.

Flexible tubing 20 extends from the needle hub for a selected distance. The embodiment of blood collection set 16 shown in FIGS. 1A and 1B depicts a 12″ length of tubing 20. An alternate blood collection set described further below includes a shorter tube. Fitting 22 is mounted to the end of tubing 20 remote from needle assembly 18. Fitting 22 shown in FIG. 1A includes a second needle assembly configured to be placed in communication with an evacuated blood collection tube. Fittings of other configurations may be provided, as explained further below.

Tray 12 of blister package 10a is molded unitarily from a thermoplastic material such as PVC or PETG. More particularly, tray 12 is molded as shown in FIGS. 4–9 to include a substantially planar bottom wall 50 and a unitary sidewall enclosure 51 extending generally upward from bottom wall 50. Sidewall enclsoure 51 comprises lateral walls 52 and 54, end walls 56 and 58 and corner walls 60 and 62. A peripheral flange 64 extends outwardly from sidewall enclosure 51 and defines a plane that is substantially parallel to bottom wall 50 and spaced from bottom wall 50 by distance "c". Distance "c" exceeds maximum height "a" of needle shield 26 as shown in FIG. 2.

Central portions of lateral walls 52 and 54 define overhangs adjacent peripheral flange 64. The overhangs define concave regions 52a and 54a at locations on lateral walls 52 and 54 adjacent bottom wall 50. Concave regions 52a and 54a are dimensional to grip a section of tubing 20, as shown in FIG. 3.

Figure 6:
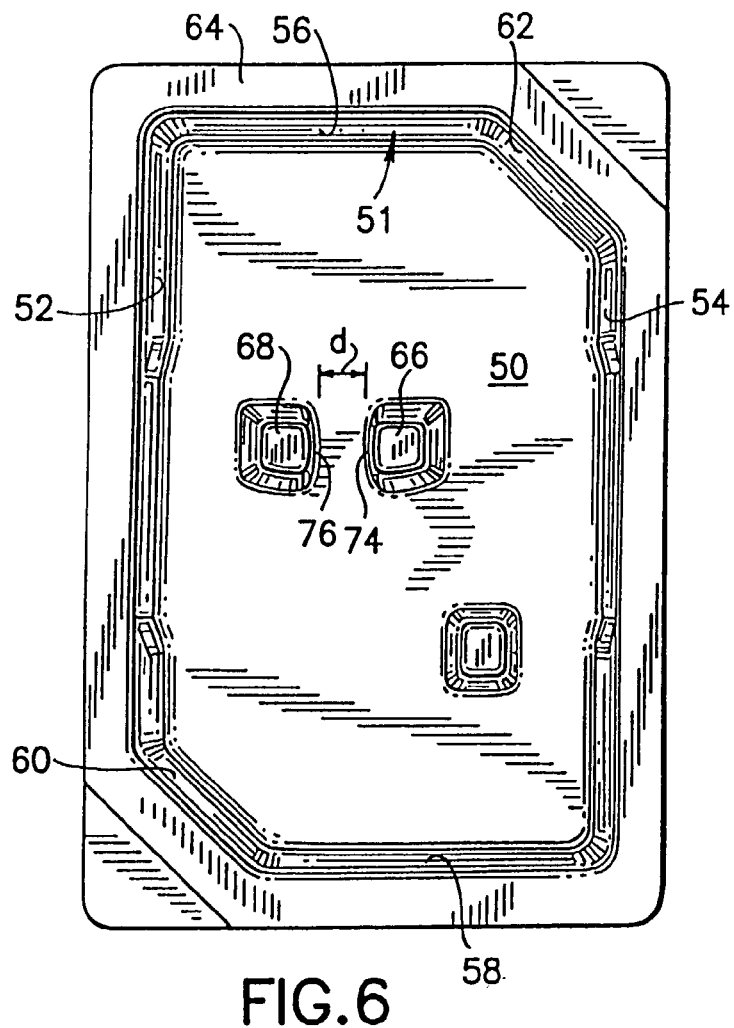
FIG. 6 is a top plan view of the tray.
Figure 7:
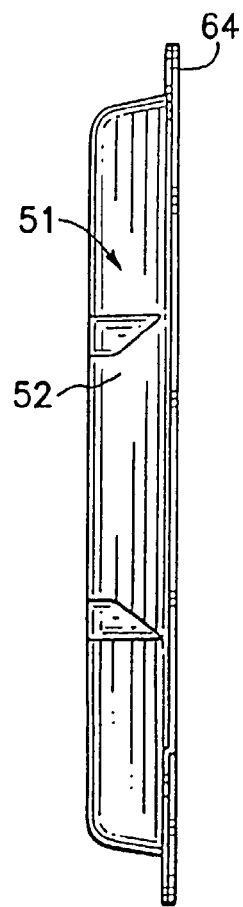
FIG. 7 is a side elevational view of the tray.
Figure 8:
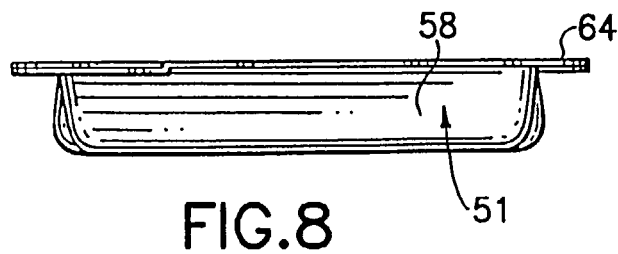
FIG. 8 is an end elevational view of the tray.
Figure 9:
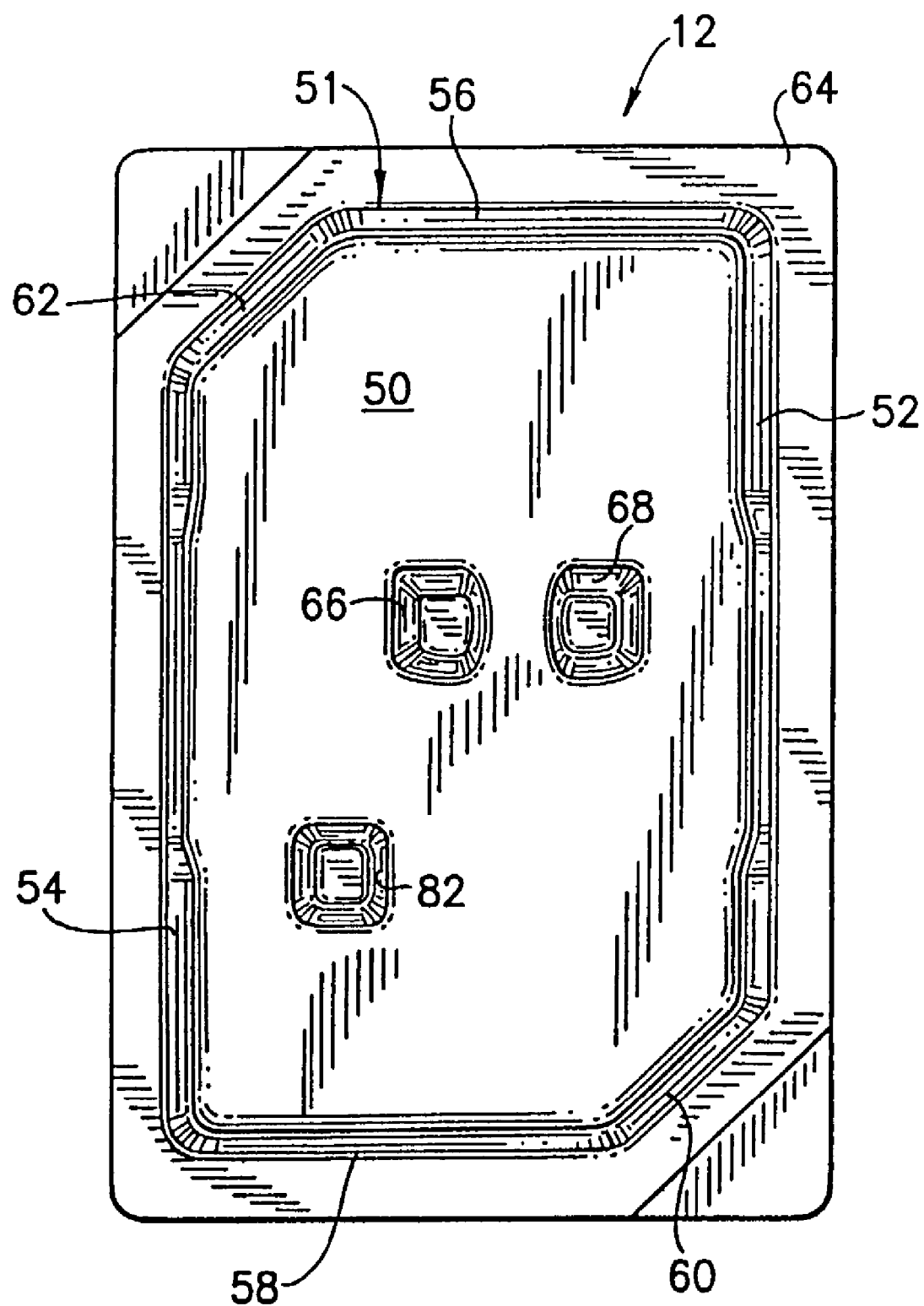
FIG. 9 is a bottom plan view of the tray.

Tray 12 is further characterized by gripping towers 66 and 68 that project upwardly from bottom wall 50 at locations spaced from one another and spaced from the sidewall enclosure 51. Gripping towers 66 and 68 include top walls 70 and 72 that are substantially coplanar with peripheral flange 64. Gripping towers 66 and 68 are further characterized by opposed facing convex walls 74 and 76 respectively. Convex walls 74 and 76 are substantially orthogonal to bottom wall 50 and are spaced from one another by a minimum distance "d" as shown in FIG. 6. Distance "d" is less than minimum width "b" on portions of safety shield 26 adjacent actuating opening 44. Gripping towers 66 and 68 further include non-gripping sidewalls 78 and 80 that are aligned to bottom wall 50 at acute angles. Thus, gripping towers 66 and 68 taper to smaller cross sections at locations further from bottom wall 50. The tapered configuration of gripping towers 66 and 68 makes gripping towers 66 and 68 resistant to deformation in response to downward forces on top walls 70 and 72. However, the convex configuration of facing walls 74 and 76 facilitates inward resilient deflection or dimpling of convex walls 74 and 76, and hence secure resilient gripping of needle shield 26.

Tray 12 is further characterized by a positioning tower 82 that projects from bottom wall 50 at a location spaced from gripping towers 66 and 68. Positioning tower 78 has a planar top wall 84 that is located below the plane defined by peripheral flange 64 in the illustrated embodiment.

Needle assembly 18 of blood collection set 16a can be mounted in tray 12 by urging the narrowed portion of safety shield 26 adjacent actuating opening 44 into the space between gripping towers 66 and 68. More particularly, needle assembly 18 is urged into tray 12 such that bottom surface 38 of safety shield 26 faces bottom wall 50 of tray 12. The necked down portion of safety shield 26 adjacent actuating opening 44 is aligned with the space between gripping towers 66 and 68. Minimum width "d" between gripping towers 66 and 68 is less than minimum width "b" of safety shield 26. Hence, opposed convex facing surfaces 74 and 76 of gripping towers 66 and 68 will deflect resiliently inwardly to grip needle assembly 18 and hold needle assembly 18 substantially adjacent bottom wall 50 of tray 12. In this position, wings 40 and 42 will be substantially adjacent and parallel to bottom wall 50. Tubing 20 then is coiled within tray 12 and substantially adjacent bottom wall 50. More particularly, tubing 20 is retained in concave spaces 52a and 54a beneath the overhang defined on lateral walls 52 and 54. Thus, the overhangs retain tubing 20 in proximity to bottom wall 50 without a separate band. Fixture 22 is disposed between lateral wall 54 and positioning tower 78. Accordingly, lateral wall 54 and positioning tower 78 limit movement of fixture 22 within tray 12.

Blister package 10a is completed by applying cover 14 to peripheral flange 64. Cover 14 is adhered or bonded removably to peripheral flange 64. Cover 14 will be supported around its periphery by peripheral flange 64. Additionally, central portions of cover 14 will be supported by top walls 70 and 72 of gripping towers 66 and 68.

Bottom wall 50 of tray 12 and central portions of cover 14 are relatively flexible and can be moved toward one another in response to digital pressure. However, gripping towers 66 and 68 are relatively rigid and resist forces that would urge central portions of cover 14 toward bottom wall 50 of tray 12. Additionally, gripping towers 66 and 68 are disposed on opposite respective sides of actuator button 46 and project from bottom wall 50 a distance "c" that is greater than the maximum height "a" of needle assembly 18. Hence, gripping towers 66 and 68 prevent inadvertent actuation of needle shield 26 that could make blood collection set 16 unusable. Additionally, gripping towers 66 and 68 releasably fix needle assembly 18 at a central position in tray 12, and therefore prevent any movement that might cause safety cap 24 to project through cover 14.

Positioning tower 82 does not perform a direct holding function. However, positioning tower 78 facilitates spooling of tubing 20 and limits movement of fitting 22.

Blood collection set 16a can be accessed merely by peeling cover 14 from peripheral flange 64 substantially in a conventional manner for blister packages. A user then grips portions of needle assembly 18 near proximal end 28 of safety shield 26 and lifts needle assembly 18 upwardly away from bottom wall 50. The resiliency of convex facing walls 74 and 76 enables needle assembly 18 to be released from gripping towers 66 and 68. Continued lifting force will cause tubing 20 to deflect and separate from recesses 52a and 54a formed by the overhang on lateral walls 52 and 54. Fitting 22 also will be moved from the space between tower 82 and sidewall 54. Thus, blood collection set 16 can be used substantially in a conventional manner.

FIG. 1B shows an alternate blister package 10b. Blister package 10b includes a tray 12 and cover 14 identical to the tray and cover described with respect to the embodiment of FIG. 1A. Blister package 10b safely holds a blood collection set 16b. Blood collection set 16b includes a needle assembly 18 and a length of tubing 20, both of which are identical to needle assembly 18 and tubing 20 described with respect to blood collection set 16a of FIG. 1A. However, blood collection set 16b includes a fitting 22b that differs from the fitting 22a described with respect to the embodiment of FIG. 1A. In particular, the fitting 22b does not include a second needle cannula and is configured for mating with other portions of an IV system.

Figure 10A:
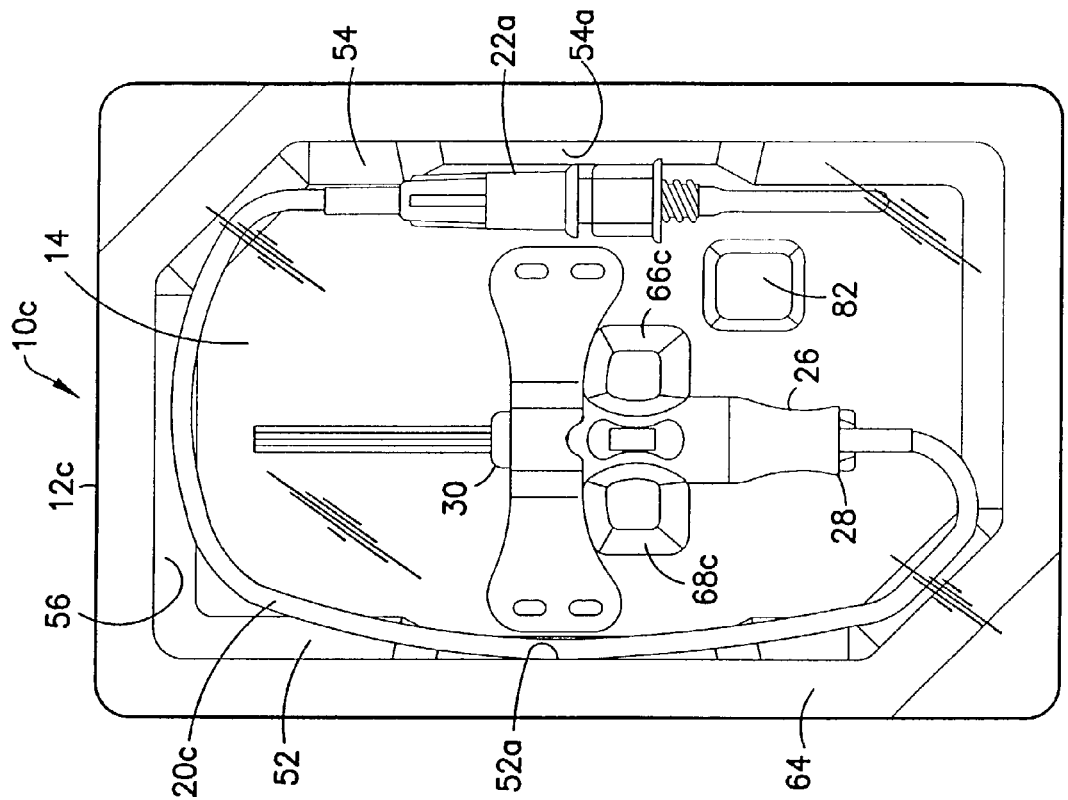
FIGS. 10A and 10B are top plan views of third and fourth blister packages of the subject invention.

Blister packages 10a and 10b shown in FIGS. 1A and 1B are intended for use with a blood collection set having a 12" length of tubing 20. Some blood collection sets, however, include a shorter length of tubing, and in particular a 7" length of tubing. FIG. 10A shows a blister package 10c for accommodating a blood collection set 16c with a needle assembly 18, a 7" length of tubing 20c, and a fitting 22. Needle assembly 18 of blister package 10c is identical to needle assembly 18 of blister package 10a shown in FIG. 1A. Fitting 22 of blister package 10c also is identical to fitting 22 of blister package 10 shown in FIG. 1A. Thus, detailed descriptions of these components are not provided.

Blister package 10c includes a tray 12c that is very similar to tray 12 in blister package 10a in FIG. 1A. However, tray 12c includes gripping towers 66c and 68c that are positioned on bottom wall 50 at a location closer to tower 82. Needle assembly 18 can be positioned between gripping towers 66c and 68c substantially as described with respect to the embodiments of FIGS. 1A and 1B. However, distal end 30 of safety shield 26 projects toward end wall 56 and away from tower 78. Tubing 20c is positioned in recesses 52a and 54a under the overhang defined on lateral wall 52. Hence, tubing 20c does not undergo a complete loop within tray 12c. However, the overhang still functions to hold tubing 20 in proximity to bottom wall 50 of tray 12c. Additionally, tower 82 functions to limit movement of fitting 22, and hence helps to keep blood collection set 20c in the coiled condition shown in FIG. 10A.

Figure 10B:
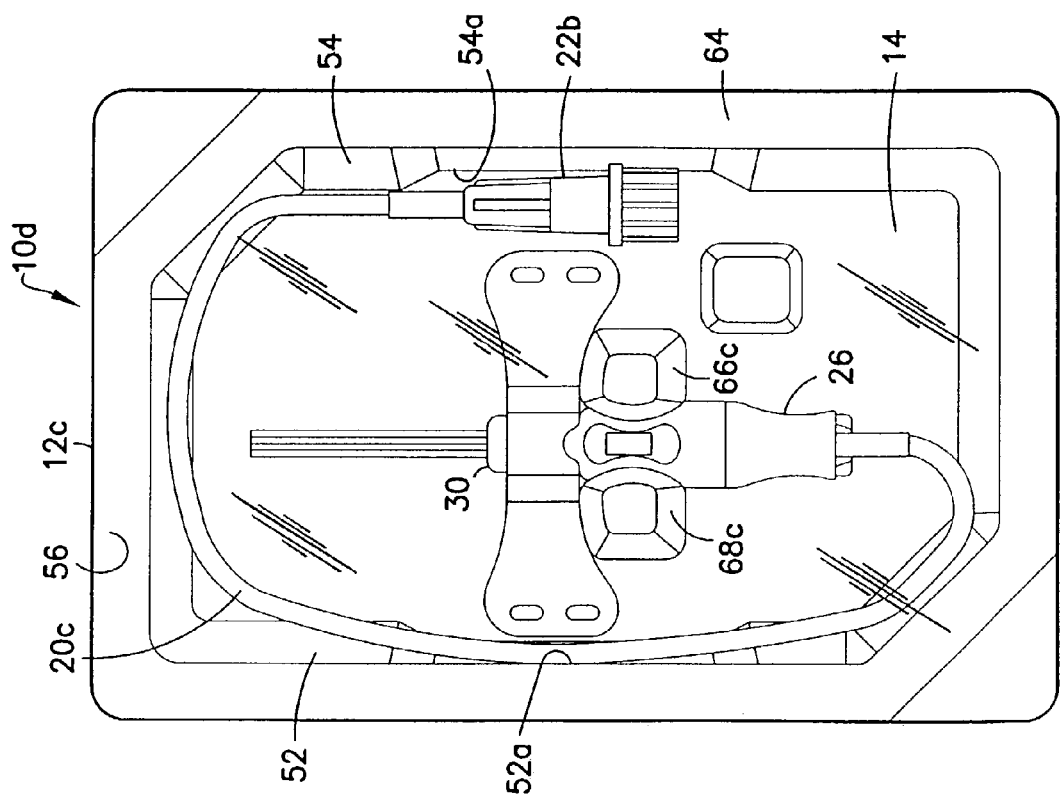

FIG. 10B shows a blister package 10d with a tray 12c identical to the tray 12c shown in FIG. 10A. Blister package 10d includes a blood collection set 16d with a needle assembly 18 and tubing 20 identical to the needle assembly and tubing of the embodiment shown in FIG. 10A. However, fitting 22b does not have a needle cannula and is identical to the fitting 22b described with respect to the embodiment of FIG. 1B.

The preceding embodiments have illustrated the tray as used with a blood collection set. However, a tray in accordance with the subject invention also can be used with a catheter insertion unit that has a spring-driven, button-actuated safety shield, or with other type of blood collection sets or catheter or guide wire insertion device.

What is claimed is:

1. A blister package comprising:
   a blood collection set with a push button and push button actuated needle safety shield mechanism, said blood collection set having a width and a height; and
   a tray unitarily molded from a plastic material and having a bottom wall, a sidewall enclosure extending upwardly from said bottom wall a distance greater than said height of said blood collection set, a peripheral flange extending outwardly from portions of said sidewall enclosure remote from said bottom wall, first and second gripping towers projecting upwardly from said bottom wall at locations spaced from said sidewall enclosure, each said gripping tower having a top wall spaced from said bottom wall a distance greater than said height of said blood collection set, said gripping towers having opposed facing gripping walls spaced from one another by distances no greater than said width of said blood collection set such that said gripping towers grip said blood collection set inserted between said gripping towers, said gripping towers and a cover secured to said peripheral flange and covering said blood collection set, being sufficiently high for preventing inadvertent actuation of said push button from outside said package.

2. The blister package of claim 1, wherein the blood collection set comprises a spring-driven safety mechanism.

3. The blister package of claim 1, wherein the bottom wall is substantially planar.

4. The blister package of claim 3, wherein the peripheral flange is substantially parallel to the bottom wall, and wherein said top walls of said gripping towers are substantially coplanar with said peripheral flange.

5. The blister package of claim 4, wherein said opposed facing walls of said gripping towers are substantially perpendicular to said bottom wall of said tray.

6. The blister package of claim 1, wherein said opposed facing walls of said gripping towers have opposed facing convex surfaces configured for mating with surfaces of said blood collection set and resiliently deflecting sufficiently for gripping said blood collection set inserted between said gripping towers.

7. The blister package of claim 6, wherein each said gripping tower includes a plurality of non-gripping sidewalls, said non-gripping sidewalls converging toward one another at further distances from said bottom wall.

8. The blister package of claim 6, wherein a plurality of portions of said sidewall enclosure converged toward one another to define an overhang, said blood collection set comprising a length of flexible tubing, said tubing being releasably engaged between said overhang and said bottom wall.

9. The blister package of claim 1, further comprising at least one non-gripping tower projecting from said bottom wall at locations spaced from said sidewalls, said non-gripping tower being disposed for positioning a portion of said blood collection set with a push button actuated needle safety shield mechanism between said non-gripping tower and one of said sidewalls.

10. The blister package of claim 1, wherein actuation of said push button occurs by a radial pressure normal to the plane of said bottom wall, and wherein said gripping towers are disposed on opposite respective sides of said push button, such that actuation which is prevented by the height and position of said gripping towers.

11. A method for packaging a blood collection set with a push button actuated needle safety shield mechanism, said method comprising:

provdiing a blood collection set with a push button and push button actuated needle safety shield mechanism with a needle assembly containing said needle safety shield, a length of tubing projecting from said needle assembly and a fitting at an end of said tubing remote from said needle assembly, portions of said needle assembly having a width and a height;

providing a molded plastic tray having a bottom wall, a plurality of interconnected sidewalls extending upwardly from said bottom wall a distance greater than said height of said needle assembly and a peripheral flange extending outwardly from said sidewalls, first and second gripping towers having tops disposed above said bottom wall a distance greater than said height of said needle assembly for preventing inadvertent actuation of said push button, said gripping towers being spaced from one another a distance no greater than said width of said needle assembly;

placing said blood collection set in said tray such that said portions of said needle assembly are between said gripping towers, with said gripping towers securely positioning said needle assembly between opposed facing sidewalls of said gripping towers; and securing a removable cover across said peripheral flange.

12. The method of claim 11, wherein at least one of said sidewalls has a concave recess adjacent said bottom wall, said step of placing said blood collection set in said tray comprising securing said tubing in said concave recess of said sidewall.

13. The method of claim 11, wherein the blood collection set comprises a spring-activated needle safety shield mechanism, and the portions of the needle assembly are in proximity to an activating element of the spring-activated needle safety shield mechanism.

14. The method of claim 11, wherein actuation of said push button which occurs by a radial pressure normal to the plane of said bottom wall and further comprising the step of placing said blood collection set in said tray such that said push button of said blood collection set is between said gripping towers, with said gripping towers securely positioning said push button between said opposed facing sidewalls of said gripping towers, such that actuation is prevented by the height and position of said gripping towers.

* * * * *